(12) United States Patent
Descouts et al.

(10) Patent No.: US 7,090,496 B2
(45) Date of Patent: Aug. 15, 2006

(54) ENDOSSEOUS IMPLANT

(75) Inventors: Pierre Descouts, Neydens (FR); Björn-Owe Aronsson, Veyrier (CH); Michael Grätzel, St Sulpice (CH); Carine Viornery, Carantec (FR); Peter Péchy, Lausanne (CH)

(73) Assignees: Universite de Geneve, Geneva (CH); Ecole Polytechnique Federale de Lausanne, Lausanne (CH)

( * ) Notice: Subject to any disclaimer, the term of this patent is extended or adjusted under 35 U.S.C. 154(b) by 328 days.

(21) Appl. No.: 10/432,025

(22) PCT Filed: Nov. 19, 2001

(86) PCT No.: PCT/EP01/13365

§ 371 (c)(1),
(2), (4) Date: Aug. 28, 2003

(87) PCT Pub. No.: WO02/40075

PCT Pub. Date: May 23, 2002

(65) Prior Publication Data

US 2004/0049287 A1    Mar. 11, 2004

(30) Foreign Application Priority Data

Nov. 20, 2000   (WO) .................. PCT/EP00/11510

(51) Int. Cl.
*A61C 8/00* (2006.01)

(52) U.S. Cl. .................... 433/201.1; 433/174

(58) Field of Classification Search ................ 433/174, 433/201.1
See application file for complete search history.

(56) References Cited

U.S. PATENT DOCUMENTS

| | | | |
|---|---|---|---|
| 5,642,996 A | * | 7/1997 | Mochida et al. ............ 433/174 |
| 5,646,134 A | | 7/1997 | Yates et al. |
| 5,733,564 A | | 3/1998 | Lehtinen et al. |

FOREIGN PATENT DOCUMENTS

| | | |
|---|---|---|
| EP | 0 860 213 | 8/1998 |
| WO | 92 09697 | 6/1992 |
| WO | 99 11202 | 3/1999 |

* cited by examiner

*Primary Examiner*—Cary E. O'Connor
*Assistant Examiner*—Candice C. Stokes
(74) *Attorney, Agent, or Firm*—Wenderoth, Lind & Ponack, L.L.P.

(57) ABSTRACT

Endosseous implant to be applied to human or animal bone, said implant having a surface made from a selected metal or a selected metal alloy or a ceramic, whereby said metal resp. metal alloy is selected from chromium, niobium, tantalum, vanadium, zirconium, aluminium, cobalt, nickel, stainless steels or an alloy thereof, said surface having a smooth or rough texture, characterized in that said surface has been treated with at least one pharmaceutically acceptable organic compound carrying at least one phosphonic acid group or a derivative thereof preferably a pharmaceutically acceptable salt or ester or amid thereof and method for producing said implant.

26 Claims, No Drawings

ENDOSSEOUS IMPLANT

The present invention relates to a selected metallic or selected ceramic endosseous implant to be applied to a human or animal bone, said implant having a smooth or rough surface texture, and wherein said surface has been treated with at least one selected organic compound carrying at least one phosphonic acid group or a derivative thereof.

Selected metallic surfaces within the meaning of the present invention are made from metals such as chromium, niobium, tantalum, vanadium, zirconium, aluminium, cobalt, nickel, stainless steels or alloys thereof. Excluded are metallic titanium and metallic titanium alloy surfaces.

Ceramic surfaces within the meaning of the present invention are preferably made from a metal oxide, metal carbide, metal nitride, metal oxynitride, metal carbonitride and/or metal oxycarbide. Examples of such metal oxides, carbides, nitrides, oxynitrides, carbonitride or oxycarbides are those of chromium, niobium, tantalum, vanadium, zirconium, aluminium, cobalt, nickel, stainless steels or alloys thereof, included also titanium carbide, titanium nitride, titanium oxynitride, titanium carbonitride and/or titanium oxycarbide.

Implants according to the present invention may be used as prostheses in medicine, more specifically in orthopaedics, for replacing or strengthening broken or diseased bones, and in dentistry, for anchoring artificial teeth and for anchoring of bone anchored hearing prosthesis. It has been shown that surfaces modified according to the present invention surprisingly enhance the bone bonding strength.

Implants which are used as prostheses in medicine for replacing or strengthening broken or diseased bones or as artificial teeth are known. These implants must be made of a non-corrosive material and must be compatible with the surrounding tissue without producing immunologic reactions effecting rejection by the body. In the following the terms "surface" or "contact surface" refer to the defined metallic or ceramic implant surface not yet treated according to the present invention and the term "modified surface" to said surface treated according to the present invention.

It is known that implanting devices in the form of screws, plates, nails, pins, and specially formed parts into the skeletal structure of humans and animals as artificial prosthetic is a means for permanent replacement of missing structural parts or as permanent anchoring devices. An excellent "osseointegration" is required for those situations where the implanted device should remain permanently adhered to the contacting bone surface.

It is known to use selected metals and selected ceramic materials for implants. When carefully produced, the implant with its surface exhibits biocompatibility in the sense that it remains passive for bone regeneration and does not per se induce adverse reactions such as inflammation or soft tissue generation or encapsulation. The interface obtained between the implant and the bone tissue normally consists of a protein layer of about 100 nm to 1 µm thickness preventing the bone tissue from being in direct molecular contact with the implant.

The actual state of the art for endosseous implants is based on different approaches, for example (i) the creation of a suitable roughness of the implant surface giving a mechanical interlocking between bone and implant and/or (ii) coating the surface of the implant, e.g. with an artificial hydroxyapatite for improving the healing process and the bone-implant intimate contact.

It is known that a high surface roughness increases the mechanical stability of the implant in the bone tissue. Mechanical surface treatment significantly alters the topography, while the surface chemistry remains substantially unchanged. The disadvantages of an implant with a high surface roughness are that a purely mechanical anchoring is very sensible to micromotions which may lead to a deterioration of the mechanical anchorage and that the osseointegration time of the implant is relatively long.

Coating the surface of the implant with an artificial hydroxyapatite decreases the osseointegration time. However, it is very difficult, if not impossible, to produce hydroxyapatite coatings with a long term stability on load bearing implants. The interface between the coating and the implant is often disrupted or the coatings are flaked off.

It has now been found that if the surface of an endosseous implant which has a selected metallic or ceramic surface as defined herein is treated with at least one organic compound carrying at least one phosphonic acid group [—P(O)(OH)$_2$] or a derivative thereof, as defined herein below, said surface shows a surprisingly improved bone bonding strength and a surprisingly shortened osseointegration time compared to the non treated surface and does not have the disadvantages as known for surfaces having a hydroxyapatite coating.

The present invention is defined in the claims. The present invention specifically refers to an endosseous implant to be applied to a human or animal bone, said implant having a surface made from a selected metal or a selected metal alloy or a ceramic, whereby said metal resp. metal alloy is selected from chromium, niobium, tantalum, vanadium, zirconium, aluminium, cobalt, nickel, stainless steels or an alloy thereof, said surface having a smooth or rough texture, characterized in that said surface has been treated with at least one pharmaceutically acceptable organic compound carrying at least one phosphonic acid group or a derivative thereof, which is preferably a pharmaceutically acceptable ester or amide or a salt thereof.

The present invention further refers to a process for producing the implant according to the present invention, which is characterized in that said surface is treated with at least one pharmaceutically acceptable organic compound carrying at least one phosphonic acid group or a derivative thereof preferably an ester or an amide or a salt thereof.

The metallic surface of the endosseous implant to be treated according to the present invention is made from chromium, niobium, tantalum, vanadium, zirconium, aluminium, cobalt, nickel, stainless steels or an alloy thereof. Such metals and metal alloys for making implants are described for example in Breme et al., Metals as biomaterials, pp. 1–71 (1998), John Wiley & Sons Ltd, Chichester, England; J. B. Park and R. S. Lakes, Biomaterials, An Introduction (1992), 2nd Edition, Plenum Press, New York) pp. 79–115 and 293–354; R. Schmidt, Comportement des matériaux dans les milieux biologiques, Applications en médecine et biotechnologie, Vol. 7 (1999) pp. 294–343, Presses polytechniques et universitaires romandes, Lausanne, Switzerland, the relevant contents of which are incorporated herein by reference.

Alternatively, the surface of the endosseous implant to be treated according to the present invention may be made of a ceramic. Such ceramic surfaces are for example metallic surfaces which have been treated thermally or chemically or treated with a plasma or another appropriate method. Such treatments are known and have been described in the literature, such as oxide surfaces, carbide surfaces, nitride surfaces, oxynitride surfaces, carbonitride surfaces or oxycarbide surfaces, for example those of chromium, niobium, tantalum, vanadium, zirconium, aluminium, cobalt, nickel, stainless steels or alloys thereof. Included are titanium carbide, titanium nitride, titanium oxynitride, titanium carbonitride and/or titanium oxycarbide. Excluded from the present invention are surfaces made from titanium oxide.

Such surfaces and their production is known and is described for example in H. Bender et al., Surf. Interface Anal. 14 (1989) pp. 337fs. Preferred ceramic surfaces which are made from metal oxides, are aluminium oxide or zirconium oxide or silicon oxide, preferably from apatites, preferably hydroxyapatite or fluoroapatite, or apatite like materials, preferably tricalciumphosphate, or brushite type layers such as are described for example in Breme et al., Metals as biomaterials, pp. 219–264 (1998), ed. J. A. Helsen et al., John Wiley & Sons Ltd, Chichester, England; or J. B. Park and R. S. Lakes, Biomaterials, An Introduction (1992), 2nd Edition, Plenum Press, New York, pp. 117–140 and 169–183; or R. Schmidt, Comportement des matériaux dans les milieux biologiques, Applications en médecine et biotechnologie, Vol. 7 (1999), pp. 306–314, Presses polytechniques et universitaires romandes, Lausanne, Switzerland).

Other ceramic surfaces which may be used within the scope of the present invention may be glass like surfaces made for example from silicate glass, or boron silica glass, or bioglass such as described for example in R. Schmidt, Comportement des matériaux dans les milieux biologiques. Applications en médecine et biotechnologie, Vol. 7 (1999), pp. 306–314, Presses polytechniques et universitaires romandes, Lausanne, Switzerland as well as in other literature references cited above. the contents of which are incorporated herein by reference.

Preferred organic compounds to be used within the scope of the present invention have at least one phosphonic acid group or a derivative thereof, which is preferably an ester or an amide or a salt thereof, resp. preferred implants have a surface which has been treated with at least one organic compound, or a mixture of such compounds, corresponding to the general formula (I):

$$A\text{-}[P(O)(OH)_2]_p \qquad (I),$$

or a pharmaceutically acceptable derivative thereof, which is preferably an ester or an amide or a salt thereof, wherein A means $A_1$ or $A_2$, and $A_1$ is a residue of a linear, branched or cyclic, saturated or unsaturated, hydrocarbon residue with n carbon atoms, whereby said residue may be substituted by hydroxyl and/or carboxyl and optionally further interrupted by one or more oxygen and/or sulphur and/or nitrogen atoms, carrying p phosphonic acid groups, wherein n is a number from 1 to 70, preferably 1 to 40, preferably 1 to 22, and p is 1, 2, 3, 4, 5 or 6, preferably 1, 2, 3, 4 or 5, preferably 1, 2, 3 or 4; or or A means $A_2$ and $A_2$ is a residue of an amino acid or of a sequence of amino acids resp. of a protein or of a polypeptide, preferably a residue of the superfamily of Transforming Growth Factor beta (TGF-β); or a residue of a specific drug molecule, wherein each residue $A_2$ carries p phosphonic acid groups, and p is 1 to 6, preferably 1, 2, 3 or 4, preferably 1, 2, or 3, when $A_2$ is a residue of an amino acid or of a sequence of amino acids resp. of a protein or of a polypeptide; or p is 1, 2, 3, 4, 5 or 6, preferably 1, 2 or 3, and preferably 1, when $A_2$ is a residue of a specific drug molecule originally not bearing any phosphonic group, optionally falling under the definition given for $A_1$.

Compounds (i) and (ii) of the general formula (I) are preferred:
(i) If A has a meaning of $A_1$, then: when n is 1 and p is 2: A is preferably —$CH_2$—; or when n is 1: p is preferably 3 or 4, preferably 3; or when n is 2 to 10: p is preferably 2, provided each phosphonic acid group or phosphonic acid ester group or phosphonic acid amide group is bound to a different carbon atom within the same molecule; or when n is 2 to 10: p is preferably 3, 4, 5 or 6, preferably 3, 4 or 5, preferably 3 or 4; or when n is 11 to 70: p is preferably 2, 3, 4, 5 or 6, preferably 2, 3, 4 or 5, preferably 2, 3 or 4.
(ii) If A has the meaning of $A_2$, then: p is preferably 1 or 3–6, preferably 1, for the case that $A_2$ is a residue of a specific drug molecule originally not bearing any phosphonic group, optionally falling under the definition given for $A_1$.

It is assumed that the phosphonate compounds as specified herein, especially as acids or salts, form a covalent bond with the surface of the implant thereby improving the osseo-integration properties of said surface to a remarkable and unexpected extent. The present invention however is not bound to this explanation.

$A_1$ preferably is a saturated hydrocarbon residue of the formula —$(C_nH_{2n+2-p})$—, wherein n means 1 to 70, preferably 1 to 40, preferably 1 to 22. Preferred is the free acid or the salt form of the compound of formula (I), preferably where the pharmaceutically acceptable salt is an alkali salt, preferably of sodium or potassium salt.

Examples of compounds of formula (I) wherein $A_1$ is a residue of a saturated hydrocarbon [e.g. an alkyl chain with 1 to 70 carbon atoms ($C_1$–$C_{70}$-Alkyl)] are monophosphonic acids such as methanephosphonic acid, ethanephosphonic acid, propane-phosphonic acid or polyphosphonic acids such as methylenediphosphonic acid, ethane-1,2-diphosphonic acid, propane-1,3-diphosphonic acid, ethane-1,1,2-triphosphonic acid, propane-1,1,3-triphosphonic acid, butane-1,1,4-triphosphonic acid, pentane-1,1,5-triphosphonic acid, pentane-2,2,5-triphosphonic acid, hexane-2,2,6-triphosphonic acid, pentane-1,1,5,5-tetraphosphonic acid, heptane-1,4,4,7-tetraphosphonic acid, propane-1,1,3,3-tetraphosphonic acid, or nonane-1,5,5,9-tetraphosphonic acid.

Examples of compounds of formula (I) wherein $A_1$ is a residue of an unsaturated hydrocarbon are unsaturated monophosphonic acids and polyphosphonic acids such as those given in H.

Fleisch, Bisphosphonates in bone disease, from the laboratory to the patient 2000, 4rd edition, The Parthenon Publishing Group, p.31–33, which compounds are incorporated herein by reference.

If the pharmaceutically acceptable ester is used, the isopropyl phosphonate or ethyl phosphonate esters, preferably of the acids given in the two previous chapters, are preferred. Further examples of such esters are: tetra isopropyl methylenediphosphonate, hexaethyl ethane-1,1,2-triphosphonate, hexaisopropyl butane-1,1,4-triphosphonate, hexaisopropyl pentane-1,1,5-triphosphonate, hexaisopropyl pentane-2,2,5-triphosphonate, hexaisopropyl hexane-2,2,6-triphosphonate, octaisopropyl propane-1,1,3,3-tetraphosphonate, octaisopropyl heptane-1,4,4,7-tetraphosphonate, octaisopropyl nonane-1,5,5,9-tetraphosphonate.

Examples of compounds of formula (I) wherein $A_2$ is a residue of a protein resp. polypeptide are compounds in the form of a Transforming Growth Factor beta (TGF-β) in which are included the all members of the superfamily of growth factors and particularly the TGF-β1, TGF-β2, TGF-β3, TGF-β4, and TGF-β5 as described for example in A. B. Roberts, M. B. Sporn, Handbook of Experimental Pharmacology, 95 (1990) pp. 419–472 or D. M. Kingsley, Genes and Development 8 (1994) p. 133–146, and references therein, where the peptide chain has been modified to contain an alkylphosphonic acid group or a derivative thereof preferably an ester or an amide or a salt thereof. In this sense the compound of formula (I) represents a Transforming Growth Factor beta (TGF-β) as defined by the members of the superfamily of growth factors, preferably the TGF-β1, TGF-β2, TGF-β3, TGF-β4, and TGF-β5, wherein each time the peptide chain has been modified to contain at least one alkylphosphonic acid group or a derivative thereof preferably an ester or an amide or a salt thereof.

Examples of compounds of formula (I) wherein A is a residue of a Bone Morphogenic Protein (BMP) (being a subfamily to the TGF family) are compounds e.g., the BMP-2 (BMP-2a), BMP-3, BMP-4 (BMP-2b), BMP-5, BMP-6, BMP-7 (OP-1), BMP-8 (OP-2), BMP-9, BMP-10, BMP-11, BMP-12, BMP-13, as found for example in J. M. Wozney et. al., Science 242 (1988) 1528–1534; A. J. Celeste et al., Proc. Natl. Acad. Sci. USA 87 (1990) 9843–9847; E. Özkaynak et al., J. Biol. Chem. 267 (1992) 25220–25227; Takao et al., Biochem. Biophys. Res. Com. 219 (1996) 656–662; WO 93/00432; WO 94/26893; WO 94/26892; WO 95/16035 and references therein, where the peptide chain has been modified to contain an alkylphosphonic acid group or a derivative thereof preferably an ester or an amide or a salt thereof. These compounds are incorporated herein by reference. In this sense the compound of formula (I) represents a Bone Morphogenic Protein (BMP), preferably the BMP-2 (BMP-2a), BMP-3, BMP-4 (BMP-2b), BMP-5, BMP-6, BMP-7 (OP-1), BMP-8 (OP-2), BMP-9, BMP-10, BMP-11, BMP-12, BMP-13, wherein the peptide chain has been modified to contain at least one alkylphosphonic acid group or a derivative thereof preferably an ester or an amide or a salt thereof.

Examples of compounds of formula (I) wherein $A_2$ is a residue of an amino acid are 2-amino-4,4-bis-(diethoxyphosphoryl)-butyric acid as described for example in O. Fabulet et al., Phosphorus, Sulphur Silicon and Related Elements, 101, 225–234 (1995); 2-amino-5-(diethoxy-phosphoryl)-pentanoic acid as described for example in I. G. Andronova et al., Russ. J. Gen. Chem. 66, 1068–1071 (1996); 2-amino-4-phosphonobutyric acid as described for example in X. Y. Jiao et al., Synth. Commun. 22, 1179–1186 (1992) and references therein. Further examples are all the principal twenty amino acids as described for example in L. Stryer, Biochemistry, 3rd edition (1988), pp. 17–22, where the amino acid is modified in an analogous way with an alkylphosphonic acid group, preferably wherein the compound of formula (I) is one of the principal twenty amino acids, preferably arginine, glycine, aspartic acid, alanine, valine, proline, serine, threonine, cysteine or lysine, wherein the amino acid has been modified to contain at least one alkylphosphonic acid group or a derivative thereof preferably an ester or an amide or a salt thereof. These compounds are incorporated herein by reference.

Examples of compounds of formula (I) wherein $A_2$ is a residue of a peptide comprise but are not limited to RGD-containing peptides, RGDS-peptides, GRGDS-peptides, RGDV-peptides, RGDE-peptides, and/or RGDT-peptides. Such peptides are described for example in Y. Hirano, J. Biomed. Materials Res., 25 (1991), pp. 1523–1534 or in WO 98/52619 and references therein. Included within the scope of the present invention are also similar peptides known to have specific biological activities such as cell attachment or cell attachment prevention, and which are prepared in analogy with the peptides as mentioned above. In this sense the compound of formula (I) is a RGD-containing peptide, preferably a RGDS-peptide, a GRGDS-peptide, a RGDV-peptide, a RGDE-peptide, and/or a RGDT-peptide, which has been modified to contain at least one alkylphosphonic acid group or a derivative thereof preferably an ester or an amide or a salt thereof.

Examples of compounds of formula (I) wherein $A_2$ is a residue of a specific drug molecule are 1-hydroxy-3-(1-pyrrolidinyl)-propylidene diphosphonic acid, or cycloheptylamino-methylene diphosphonic acid, or 1-hydroxy-2-imidazo-(1,2-a)-pyridin-3-yl-ethylidene diphosphonic acid or 1-hydroxy-2-(3-pyridinyl)-ethylidene diphosphonic acid or (4-chlorophenyl)thio-methylene diphosphonic acid or 1-hydroxy-2-(1H-imidazole-1-yl)ethylidene diphosphonic acid and related compounds as described for example in H. Fleisch, Bisphosphonates in bone disease, from the laboratory to the patient 2000, 4rd edition, The Parthenon Publishing Group, pp. 31–33, and references therein. Such compounds are included herein by reference.

Preferred compounds of formula (I) are those containing a residue $A_2$ as defined above, preferably a residue of an amino acid or of a sequence of amino acids resp. of a protein or of a polypeptide, preferably a residue of the superfamily of Transforming Growth Factor beta (TGF-β), preferably a Bone Morphogenic Protein (BMP).

The following steps are recommended to be taken for producing the implant according to the present invention, i.e. for treating the surface of the implant with at least one compound of formula (I) or a mixture of these compounds. The implant is first cleaned in a cleaning bath for removing unwanted molecules resp. impurities from the surface. Preferably the implant is first treated with a degreasing agent, for example an organic solvent such as alcohol, chloroform, and another organic solvent and/or an inorganic detergent such as an aqueous alkaline solution based on sodium hydroxide or potassium hydroxide. Subsequently, the implant is carefully rinsed in pure water, preferably in distilled ultra-pure water, having preferably a conductivity resistance of at least 15 Mohm*cm. After cleaning and rinsing, the implant is dried with flowing nitrogen gas or flowing dry or hot air and stored under controlled conditions. Alternatively after degreasing the implant can be further treated in a glow-discharge plasma for cleaning the surface. The clean surface of the implant is then treated with at least one compound of formula (I) or an ester or a salt thereof, i.e. with at least one such compound or a mixture of such compounds. The compound or the mixture of said compounds is brought onto the surface of the implant by any suitable means, like brushing, spraying, dipping or, evaporation, including glow-discharge plasma assisted vapour deposition. The phosphonic acid compound or the ester or the salt thereof is preferably dissolved in a polar solvent, so that a solution with a concentration of from about $1.0 \times 10^{-5}$ mol/10 ml to $5 \times 10^2$ mol/10 ml, preferably from about $5 \times 10^{-4}$ mol/10 ml to $2.0 \times 10^{-2}$ mol/10 ml with reference to the weight of the solvent is obtained. Preferably the concentration is such that a partial or full (1% to 100%, preferably 50% to 100% of a) monomolecular layer is formed on the implant surface. The preferred solvent is pure distilled water. The implant is left in contact with the solution for a sufficiently long time, preferably for a few minutes up to a few hours. After that the implant is carefully rinsed with pure water and packed with a plastic or metallic clean packaging material preferably into an air tight packaging which preferably is evacuated or filled with an inert gas such as nitrogen or an inert liquid such as pure water as defined herein above. Said pure water may contain inorganic salts, preferably alkali salts, such as alkali chlorides, sulphates, phosphates, phosphonates, preferably the sodium and/or potassium salts, and/or compounds of the formula (I) or an ester or a salt thereof, which is preferably in a concentration of from about $1.0 \times 10^{-5}$ mol/10 ml to $5 \times 10^{-2}$ mol/10 ml, preferably from about $5 \times 10^{-4}$ mol/10 ml to $2.0 \times 10^{-2}$ mol/10 ml of solvent, which preferably is distilled water.

Analytical investigations, e.g. X-ray Photoelectron Spectros-copy analysis (XPS) or NMR, have shown that on contacting the phosphonic acid compound of formula (I) with the surface of the implant, immediate adsorption takes place. A strong bond is formed between the surface and the phosphonic acid compound so that a chemical surface modification is obtained. Several different polyphosphonic acids, salts, esters and amides as mentioned herein above were synthesized. Dental implants produced with these compounds according to the present invention have shown excellent results.

Implants according to the present invention may be in the form of screws, plates, nails, pins, and specially formed parts and may be used as prostheses in medicine, more specifically in orthopaedics, for replacing or strengthening broken or diseased bones, and in dentistry, for anchoring artificial teeth and for anchoring of bone anchored hearing prosthesis into the skeletal structure of humans and animals. The surface area of the implant which is to be bound to the body tissue resp. bones, may have a smooth or rough surface texture. Such surface textures are known and can be obtained for example by treating the surface mechanically and/or with acids and/or electrolytically and/or with a glow-discharge plasma and/or plasma spraying and/or or by electro machining. Such materials and processes have been described in different publications, for example in B.-O. Aronsson et al., J. Biomed. Mater. Res. 35 (1997), pp. 49f., the contents of which are incorporated herein by reference.

The compounds according to the general formula (I), wherein p is 3 to 6, preferably 3 or 4, and n is 4 to 70, preferably 4 to 40, preferably 4 to 22, the salts or esters or amides thereof are new. Examples of such compounds are butane-1,1,4-triphosphonic acid, pentane-1,1,5-triphosphonic acid, pentane-2,2,5-triphosphonic acid, hexane-2,2,6-triphosphonic acid, pentane-1,1,5,5-tetraphosphonic acid, heptane-1,4,4,7-tetraphosphonic acid, or nonane-1,5,5,9-tetraphosphonic acid.

The compounds hexaisopropyl butane-1,1,4-triphosphonate and octaisopropyl heptane-1,4,4,7-tetraphosphonate, resp. a mixture of these compounds, are obtained in that an alkalimetal, preferably sodium, tetra lower alkyl methylenediphosphonate, preferably tetraisopropyl methylenediphosphonate, is reacting with at least a stoichiometric amount of a dihalomethane, preferably dibromomethane, in the presence of an organic solvent having no active hydrogen atoms, preferably dry hexane or benzene or toluene.

The reaction is preferably carried out at a temperature within the range of 30° C. to 125° C., preferably 40° C. to 110° C., until the reaction is completed, which generally is within a time period of 10 to 48 hours, preferably 18 to 36 hours.

To the reaction product is then added the purified product of triisopropylphosphite that has been reacted with diisopropyl-3-bromopropane. The obtained mixture of compounds can then be separated in a conventional manner, for example by column chromatography.

In an analogous way, by reacting 1,4-dibromobutane in excess molar ratio in the range 1:6 to 1:0.5 with triisopropylphosphite, surprisingly the new compounds hexaisopropyl pentane-1,1,5-triphosphonate and octaisopropyl nonane-1,5,5,9-tetraphosphonate are produced. Further, in an analogous way the hexaisopropyl pentane-2,2,5-triphosphonate and hexaisopropyl hexane-2,2,6-triphosphonate were obtained by reacting equal parts of tetraisopropylethane-1,1-diphosphonate with diisopropyl-3-bromopropylphosphonate.

The process is further characterised by that these products are hydrolysed to produce the analogous acids by refluxing them in molar excess of HCl for a time comprised within 1 to 12 hours, preferably 1 to 6 hours. The compounds are then preferably dried under vacuum over $P_2O_5$.

The following Examples illustrate but do not limit the present invention.

EXAMPLE 1

Synthesis of Alkane Polyphosphonic Acids

Methylenediphosphonic acid was synthesized according to U.S. Pat. No. 3,400,176 and B. A. Arbusov, Pure Appl. Chem. 9 (1967), pp. 307–353 and references therein. The compound was characterized by NMR ($^1H$, $^{31}P$, $^{13}C$) mass spectroscopic elemental analysis and by its melting point. All these data are in accordance with the literature O. T. Quimby et al., Metalated methylendiphosphonate esters, preparation, characterization and synthetic applications, J. of Organomet. Chem. 13, 199–207 (1968).

Propane-1,1,3,3-tetraphosphonic acid was synthesized from tetraisopropyl methylenediphosphonate. The tetraphosphonic acidic solution was concentrated under vacuum, dried over $P_2O_5$ under vacuum. The $^1H$, $^{31}P$ and $^{13}C$ NMR results ($D_2O$) are in accordance with the given literature data.

In an analogous manner propane-1,3-diphosphonic acid, ethane-1,1,2-triphosphonic acid, butane-1,1,4-triphosphonic acid, pentane-1,1,5-triphosphonic acid, pentane-2,2,5-triphosphonic acid, hexane-2,2,6-triphosphonic acid, pentane-1,1,5,5-tetraphosphonic acid or heptane-1,4,4,7-tetraphosphonic acid, are synthesized.

EXAMPLE 2

A) A dental implant made from titanium in the form of a screw, having a diameter of 4 mm and a length of 10 mm, is produced in a conventional manner. The surface to be implanted into the body is provided with a surface roughness according to EP 0 388 575 by sandblasting the surface using an average grain size of 0.25–0.5 mm, followed by a treatment with a mixture of an aqueous acidic mixture containing a mixture of hydrochloric acid/sulfuric acid/water in a ratio of 2:1:1, at a temperature of about 80° C. for about 5 minutes so that a rough surface of the implant is obtained which is about 3.6 times larger compared to the polished surface, as measured with the voltametric method in aqueous electrolyte with 0.15M NaCl. The surface of the implant is then chemically treated with a nitrogen plasma to yield a titanium nitride surface as described in B.-O. Aronsson et al., J. Biomed. Mater. Res. 35 (1997), pp. 49f. The treated implant, resp. surface, is sonicated in bidistilled water during 15 minutes at 30° C., washed with pure water followed by sonication in water (three times) for 10 minutes and then rinsed with pure hexane and dried under vacuum (10 mm Hg, room temperature).

B) The implant as produced in chapter A) above is then put into an aqueous solution of (i) methylenediphosphonic acid [$1,5 \times 10^{-3}$ mol per 10 ml of distilled water], (ii) ethane-1,1,2-triphosphonic acid [$6.2 \times 10^{-4}$ mol/10 ml, in distilled water], (iii) pentane-1,1,5-triphosphonic acid [$1.2 \times 10^{-4}$ mol/ 10 ml, in distilled water], (iv) pentane-1,1,5-triphosphonic acid potassium salt [$1.2 \times 10^{-4}$ mol/10 ml, in distilled water] and left there at room temperature for 15 minutes. The implant is then rinsed with pure water.

The implant prepared according to the preparations B(i), B(ii), B(iii) and B(iv) are implanted into the upper jaw of a mini pig. The osseointegration is measured as the torque needed to unfasten the implant from the jaw where it had osseointegrated. Comparative test results are given for the untreated implant. The results are given in Table 1. Analogous results are obtained for further phosphonic acids given herein above. Analysis with XPS and ToF-SIMS indicated that a molecular (mono) layer was formed on the implant surface as well as on the titanium nitride surface, and that the roughness of the surface did not seem to influence this behaviour.

TABLE 1

| Preparation | Torque* after 2 weeks (Ncm) | torque* after 3 weeks (Ncm) | torque* after 4 weeks (Ncm) |
|---|---|---|---|
| B(i) | 31 | 72 | 130 |
| B(ii) | 30 | 80 | 125 |
| B(iii) | 32 | 79 | 132 |
| B(iv) | 29 | 83 | 124 |
| Comparative Test | 20 | 60 | 100 |

*the torque is given in Ncm as an average value from three measurements for each test.

The results illustrate the improved osseointegration of the implants according to the present invention compared to the non treated implants.

EXAMPLE 3

Example 2 is repeated with the difference that the original titanium surface of the implant is treated with methane in an argon glow discharge plasma so that a surface of titanium carbide is obtained. The treatment is performed as described in B.-O. Aronsson et al., J. Biomed. Mater. Res. 35 (1997), pp. 49f. Analogous test results are obtained analogous to those given in Table 1.

EXAMPLE 4

Example 2 is repeated with the difference that the implant is made of zirconium, having a zirconium oxide surface, and that the compound according to formula (I) is ethane-1,1, 3-triphosphonic acid which has been modified by linking the amine terminus of a Glycine molecule to one of the phosphonate groups. Analogous test results are obtained as given in Table 1.

EXAMPLE 5

Examples 2 and 3 are repeated with the difference that the compound according to formula (I) is the ethane-1,1,3-triphosphonic acid which is modified by linking the amine terminus of a GRGDS cell binding polypeptide to one of the phosphonate groups. Analogous results are obtained as given in Table 1.

EXAMPLE 6

Examples 2 and 3 are repeated with a the difference that the compound according to formula (I) is ethane-1,1,3-triphosphonic acid which is modified by linking the amine terminus (Methionine) of a human Bone Morphogenic Protein type 2 (BMP-2) to one of the phosphonate groups, which gives analogous test results as given in Table 1.

The invention claimed is:

1. An endosseous implant suitable for application to a human or animal bone, said implant having a surface made from a selected metal or a selected metal alloy or a ceramic, whereby said metal resp. metal alloy is selected from chromium, niobium, tantalum, vanadium, zirconium, aluminium, cobalt, nickel, stainless steels or an alloy thereof, said surface having a smooth or rough texture, wherein said surface has a layer formed thereon of at least one pharmaceutically acceptable organic compound carrying at least one phosphonic acid group or a derivative thereof, which is a pharmaceutically acceptable ester, amide or salt thereof, corresponding to the formula (I):

wherein A means $A_1$ or $A_2$, and
$A_1$ is a residue of a linear, branched or cyclic, saturated or unsaturated, hydrocarbon residue with n carbon atoms, whereby said residue may be substituted by carboxyl and optionally further interrupted by one or more oxygen and/or sulphur and/or nitrogen atoms, carrying p phosphonic acid groups, wherein
n is a number from 1 to 70, and
p is 1, 2, 3, 4, 5 or 6, or
A means $A_2$ and
$A_2$ is a residue of an amino acid or of a sequence of amino acids respectively of a protein or of a polypeptide; or a residue of a specific drug molecule, wherein each residue $A_2$ carries p phosphonic acid groups, and
p is 1 to 6, when $A_2$ is a residue of an amino acid, of a sequence of amino acids, of a protein or of a polypeptide; or
p is 1, 2, 3, 4, 5 or 6, when $A_2$ is a residue of a specific drug molecule originally not bearing any phosphonic group, optionally falling under the definition given for $A_1$.

2. The implant according to claim 1, wherein the surface of the implant is made of a ceramic selected from oxide surfaces, carbide surfaces, nitride surfaces, oxynitride surfaces, carbonitride surfaces and oxycarbide surfaces of chromium, niobium, tantalum, vanadium, zirconium, aluminium, cobalt, nickel, stainless steels or alloys thereof.

3. The implant according to claim 1, wherein the surface of the implant is made of titanium carbide, titanium nitride, titanium oxynitride, titanium carbonitride and/or titanium oxycarbide.

4. The implant according to claim 1, wherein the surface of the implant is made from a metal oxide or an apatite material.

5. The implant according to claim 1, wherein the surface of the implant is made of a glass material.

6. The implant according to claim 1, wherein
n in residue $A_1$ is a number from 1 to 40, and
p in formula (1) is 1, 2, 3, 4 or 5; or
p is 1, 2, 3 or 4, when $A_2$ is a residue of an amino acid or of a sequence of amino acids, of a protein or of a polypeptide; or
p is 1, 2 or 3, when $A_2$ is a residue of a specific drug molecule originally not bearing any phosphonic group, optionally falling under the definition given for $A_1$.

7. The implant according to claim 1, wherein A has a meaning of $A_1$, and: when n is 1 and p is 2: A is —$CH_2$—; or when n is 1: p is 3 or 4; or when n is 2 to 10: p is 2, provided each phosphonic acid group or phosphonic acid ester group is bound to a different carbon atom within the same molecule; or when n is 2 to 10: p is 3, 4, 5 or 6; or when n is 11 to 70: p is 2, 3, 4, 5 or 6.

8. The implant according to claim 1, wherein A has a meaning of $A_2$, and: p is 1 or 3–6, for the case that $A_2$ is a residue of a specific drug molecule originally not bearing any phosphonic group, optionally falling under the definition given for $A_1$.

9. The implant according to claim 1, wherein $A_1$ is a saturated hydrocarbon residue of the formula —$(C_nH_{2n+2-p})$—, wherein n means 1 to 70.

10. The implant according to claim 1, wherein the compound of formula (I) is an alkali salt.

11. The implant according to claim 1, wherein the compound of formula (I) is selected from a saturated monophosphonic acid, a saturated polyphosphonic acid, an unsaturated monophosphonic acid and an unsaturated polyphosphonic acid.

12. The implant according to claim 1, wherein the pharmaceutically acceptable ester is an isopropyl phosphonate or ethyl phosphonate ester.

13. The implant according to claim 12, wherein the ester is selected from tetra isopropyl methylenediphosphonate, hexaethyl ethane-1,1,2-triphosphonate, hexaisopropyl butane-1,1,4-triphosphonate, hexaisopropyl pentane-1,1,5-triphosphonate, hexasopropyl pentane-2,2,5-triphosphonate, hexaisopropyl hexane-2,2,6-triphosphonate, octaisopropyl propane-1,1,3,3-tetraphosphonate, octaisopropyl heptane-1,4,4,7-tetraphosphonate, and octaisopropyl nonane-1,5,5,9-tetraphosphonate.

14. The implant according to claim 1, wherein the compound of formula (I) represents a Transforming Growth Factor beta (TGF-β) as defined by members of the superfamily of growth factors, selected from TGF-β1, TGF-β2, TGF-β3, TGF-β4, and TGF-β5, wherein in each member the peptide chain has been modified to contain at least one alkylphosphonic acid group or a derivative thereof.

15. The implant according to claim 1, wherein the compound of formula (I) represents a Bone Morphogenic Protein (BMP), selected from BMP-2 (BMP-2a), BMP-3, BMP-4 (BMP-2b), BMP-5, BMP-6, BMP-7 (OP-1), BMP-8 (OP-2), BMP-9, BMP-10, BMP-11, BMP-12, BMP-13, wherein the peptide chain has been modified to contain at least one alkylphosphonic acid group or a derivative thereof.

16. The implant according to claim 1, wherein the compound of formula (I) is selected from 2-amino-4,4-bis-(diethoxy-phosphoryl)-butyric acid, 2-amino-5-(diethoxy-phosphoryl)-pentanoic acid and/or 2-amino-4-phosphonobutyric acid.

17. The implant according to claim 1, wherein the compound of formula (I) is selected from one of the principal twenty amino acids, wherein the amino acid has been modified to contain at least one alkylphosphonic acid group or a derivative thereof.

18. The implant according to claim 1, wherein the compound of formula (I) is a RGD-containing peptide, selected from a RGDS-peptide, a GRGDS-peptide, a RGDV-peptide, a RGDE-peptide, and/or a RGDT-peptide, which has been modified to contain at least one alkylphosphonic acid group or a derivative thereof.

19. The implant according to claim 1, wherein the compound of formula (I) is selected from 1-hydroxy-3-(1-pyrrolidinyl)-propylidene diphosphonic acid, cycloheptylamino-methylene diphosphonic acid, 1-hydroxy-2-imidazo-(1,2-a)-pyridin-3-yl-ethylidene diphosphonic acid, 1-hydroxy-2-(3-pyridinyl)-ethylidene diphosphonic acid, (4-chlorophenyl)thio-methylene diphosphonic acid and 1-hydroxy-2-(1H-imidazole-1-yl)ethylidene diphosphonic.

20. The implant according to claim 1 in the form of a screw, plate, nail, or pin.

21. A process for producing the implant according to claim 1, which comprises treating said surface with at least one pharmaceutically acceptable organic compound of formula (I) or a salt or ester or an amide thereof, to form said layer thereon.

22. An air tight plastic or metallic packaging material which optionally is evacuated or filled with an inert gas or an inert liquid containing an implant according to claim 20.

23. A packaging material according to claim 22, wherein said packaging material is filled with pure water containing an inorganic salt and/or a compound of formula (I) or a salt or ester thereof.

24. A packaging material according to claim 23, wherein the concentration of inorganic salt and/or a compound of formula (I) or a salt or ester thereof is from about $1.0 \times 10^{-5}$ mol/10 ml to $5 \times 10^{-2}$ mol/10 ml of the water.

25. A compound of formula (I) or salt or ester thereof according to claim 1, wherein p is 3 to 6, and n is 4 to 70.

26. The compound according to claim 25, selected from butane-1,1,4-triphosphonic acid, pentane-1,1,5-triphosphonic acid, pentane-2,2,5-triphosphonic acid, hexane-2,2,6-triphosphonic acid, pentane-1,1,5,5-tetraphosphonic acid, heptane-1,4,4,7-tetraphosphonic acid, nonane-1,5,5,9-tetraphosphonic acid, a salt thereof, an ester thereof and an amide thereof.

* * * * *